(12) United States Patent
Hoernig et al.

(10) Patent No.: US 8,594,274 B2
(45) Date of Patent: Nov. 26, 2013

(54) METHOD TO SHOW A CONCENTRATION OF A CONTRAST AGENT IN A PREDETERMINED VOLUME SEGMENT BY MEANS OF TOMOSYNTHESIS, AND CORRESPONDING TOMOSYNTHESIS APPARATUS

(75) Inventors: Mathias Hoernig, Erlangen (DE); Thomas Mertelmeier, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 81 days.

(21) Appl. No.: 13/252,334

(22) Filed: Oct. 4, 2011

(65) Prior Publication Data

US 2012/0134464 A1 May 31, 2012

(30) Foreign Application Priority Data

Oct. 4, 2010 (DE) .......................... 10 2010 041 920

(51) Int. Cl.
*A61B 6/00* (2006.01)
*H05G 1/64* (2006.01)
*G06K 9/00* (2006.01)

(52) U.S. Cl.
USPC ............. 378/22; 378/98.8; 382/128; 382/130

(58) Field of Classification Search
USPC .............................. 378/4, 8, 22, 98.8; 382/130
See application file for complete search history.

(56) References Cited

U.S. PATENT DOCUMENTS

| | | | |
|---|---|---|---|
| 4,662,379 A * | 5/1987 | Macovski ...................... | 600/428 |
| 6,950,493 B2 * | 9/2005 | Besson ............................ | 378/16 |
| 7,218,702 B2 * | 5/2007 | Mistretta et al. ................. | 378/21 |
| 7,899,152 B2 * | 3/2011 | Boese et al. ..................... | 378/19 |
| 2004/0114706 A1 * | 6/2004 | Ikeda et al. ........................ | 378/4 |
| 2006/0050840 A1 * | 3/2006 | Ikeda et al. ........................ | 378/8 |
| 2006/0067473 A1 * | 3/2006 | Eberhard et al. .............. | 378/98.9 |
| 2008/0130824 A1 * | 6/2008 | Fujisawa ........................... | 378/4 |
| 2008/0144767 A1 * | 6/2008 | Eberhard et al. ................ | 378/22 |
| 2009/0022265 A1 * | 1/2009 | Takase et al. ..................... | 378/8 |
| 2009/0028289 A1 * | 1/2009 | Tsuyuki et al. ................... | 378/8 |
| 2009/0028405 A1 * | 1/2009 | Degani et al. ................. | 382/131 |
| 2009/0028409 A1 * | 1/2009 | Tsukagoshi et al. .......... | 382/131 |
| 2009/0092225 A1 * | 4/2009 | Boese et al. ..................... | 378/19 |
| 2009/0129536 A1 * | 5/2009 | Ichihara et al. ................... | 378/4 |
| 2009/0304253 A1 * | 12/2009 | Puong et al. .................. | 382/131 |

OTHER PUBLICATIONS

"Contrast-Enhanced Digital Mammography: Initial Clinical Experience," Jong et al., Radiology (2003) pp. 842-850.
"Dual-Energy Contract-Enhanced Digital Subtraction Mammography: Feasibility," Lewin et al., Radiology (2003) pp. 261-268.
"Initial Clinical Experience With Contrast-Enhanced Digital Breast Tomosynthesis," Chen et al., Acad. Radiol. (2007) pp. 229-238.

* cited by examiner

*Primary Examiner* — Alexander H Taningco
(74) *Attorney, Agent, or Firm* — Schiff Hardin LLP (57) ABSTRACT

In an imaging method and a tomosynthesis apparatus, a two-dimensional low-energy image of the predetermined volume segment is obtained after administration of a contrast agent, followed by a two-dimensional high-energy image and then a high-energy tomosynthesis of the predetermined volume segment is obtained with a high total radiation dose that is significantly higher than the low radiation dose. The two-dimensional low-energy image is subtracted from the two-dimensional high-energy image to generate a result with which the concentration of the contrast agent is visible. Additionally, in a time interval in which an enrichment or a washing-out of the contrast agent occurs within the predetermined volume segment, a tomosynthesis of the predetermined volume segment is automatically implemented to show the concentration of the contrast agent in the predetermined volume segment.

20 Claims, 6 Drawing Sheets

METHOD TO SHOW A CONCENTRATION OF A CONTRAST AGENT IN A PREDETERMINED VOLUME SEGMENT BY MEANS OF TOMOSYNTHESIS, AND CORRESPONDING TOMOSYNTHESIS APPARATUS

BACKGROUND OF THE INVENTION

1. Field of the Invention

The present invention concerns a method to show a concentration of a contrast agent or the course of the concentration of the contrast agent in a predetermined volume segment by means of a tomosynthesis, as well as a correspondingly designed tomosynthesis apparatus.

2. Description of the Prior Art

To differentiate malignant and benign lesions or tumors, it is known to administer a contrast agent TO the volume segment to be examined and to produce a corresponding evaluation of the lesion or the tumor using the dynamic of the contrast agent concentration. Particularly in the case of malignant tumors, an enrichment of the contrast agent in the tumor (which normally takes place very quickly (within approximately 1 min)) occurs due to the neovascularization. A fast imaging is required in order to measure this increase in the contrast agent concentration. A tomosynthesis scan typically lasts up to 25 s, and when the contrast agent concentration within the volume segment to be shown changes very significantly in the enrichment phase during this time this leads to problems in the reconstruction since inconsistent data from the different angles (due to the temporally varying contrast agent concentration) are acquired during the tomosynthesis scan.

SUMMARY OF THE INVENTION

An object of the present is to better show or measure the contrast agent concentration and/or the course of the contrast agent concentration than is possible according to the prior art.

The object is achieved in accordance with the scope of the present invention by a method to show a concentration of a contrast agent in a predetermined volume segment of an examination subject by means of a tomosynthesis apparatus. After a (most often intravenous) administration of the contrast agent, the method includes the following steps:

Create a two-dimensional, low-energy image (mammography) of the predetermined volume segment with a low x-ray energy or, low x-ray dose (in a range from 20 to 35 kVp, for example). The low energy image is in particular thereby created in a standard screening projection (CC or MLO) or, more rarely, as a diagnostic exposure (spot compression, magnification mammography). Given the CC alignment ("cranial-caudal", from head to foot), the x-rays are generated such that the x-ray tube (for example) is aligned such that the x-rays travel vertically. In contrast to this, given the MLO alignment ("mediolateral oblique") the x-rays run with a defined angle relative to the vertical alignment.

Generate one or more two-dimensional high-energy images (mammography) of the predetermined volume segment with a high x-ray energy (in a range from 40 to 50 kVp) that is significantly higher than the low x-ray energy of the low-energy image. The high-energy image or images is/are generated after the low-energy image, with the alignment to generate the high-energy image or images being the same as the alignment in the generation of the low-energy image.

Implement a high-energy tomosynthesis of the predetermined volume segment.

Automatically subtract the two-dimensional low-energy image from the at least one two-dimensional high-energy image. If it is only one high-energy image, the low-energy image is subtracted with weighting from this high-energy image. Given multiple high-energy images, the low-energy image is subtracted with weighting from each of these high-energy images. A resulting image in which the concentration of the contrast agent is visible is generated by this subtraction. This subtraction is also designated as a non-temporal dual-energy subtraction (or "dual-energy subtraction").

Image data of an earlier low-energy tomosynthesis which was implemented before the administration of the contrast agent are subtracted from image data of the high-energy tomosynthesis, which is also known as a temporal dual-energy subtraction.

While the spectrum (more precisely the focal point of the spectrum) of the x-rays for generation of the high-energy images is markedly above the k-edge of the contrast agent, the spectrum (more precisely the focal point of the spectrum) of the x-rays to generate the low-energy image is markedly below this k-edge. Given the use of an iodine contrast agent, a tube voltage of well above 33 kVp (the iodine absorption edge and k-edge are at 33 kV) is used to generate a high-energy image and a tube voltage of well below 33 kVp is used to generate a low-energy image. (Given the use of gadolinium as a contrast agent, a markedly harder radiation would in particular have to be used to generate the high-energy image in comparison to iodine, for example.) The x-ray photons in the generation of the high-energy image have a sufficient amount of energy in order to strip an electron of a contrast agent atom from the k-shell, such that the contrast agent absorbs at least a portion of the x-ray radiation. In contrast to this, given the generation of the low-energy image the x-ray photons (for the most part) have insufficient energy to strip an electron of a contrast agent atom from the k-shell, such that the x-ray radiation is not absorbed by the contrast agent.

The individual projections of the high-energy tomosynthesis are similarly generated with an x-ray radiation whose spectrum lies well above the k-edge of the contrast agent, while the individual projections of the low-energy tomosynthesis are generated with an x-ray radiation whose spectrum is well below this k-edge. Since the x-ray energy or, respectively, dose is normally determined from the product of the high voltage (with which the x-ray tube operates), the tube current and the acquisition duration (switching time), the tube voltage (and therefore the energy of the individual x-ray photons) to acquire a single image and to acquire a projection of a tomosynthesis can be the same, but nevertheless the x-ray dose to generate the projection can be markedly lower than the x-ray dose to generate the single image.

There are multiple possibilities in order to subtract the image data of the low-energy tomosynthesis scan from the image data of the high-energy tomosynthesis scan:

The projections of the low-energy tomosynthesis scan are registered (possibly with the use of an angle interpolation) with the corresponding projections of the high-energy tomosynthesis scan, and then a subtraction of the respective projection of the low-energy tomosynthesis scan from the respective projection of the high-energy tomosynthesis scan is implemented, wherein a reconstruction of slice images can thereby be produced.

A defined slice within the predetermined volume segment is reconstructed from the low-energy tomosynthesis scan while a three-dimensional model of the predetermined volume segment is created from high-energy tomosynthesis scan, which model also contains information per voxel about the contrast agent content per point in time. Slice images of the defined slice are reconstructed from this three-dimensional model at respective different points in time, which slice images then respectively contain information about the contrast agent content corresponding to the point in time. Stated in a different way, a reconstruction is implemented first and then a subtraction of the (in particular registered and motion-corrected) slices.

The method according to the invention accordingly combines the temporal dual-energy subtraction of tomosynthesis results with the non-temporal dual-energy subtraction of two-dimensional images. As used herein, a dual-energy subtraction is a subtraction of first and second image data, with the first image data being generated with a higher x-ray energy than the second image data. For this reason the method is also called a two-spectra method since the x-ray radiation to generate the low-energy image data and the x-ray radiation to generate the high-energy image data have different wavelengths. Stated differently, the dual-energy subtraction designates the subtraction of a low-energy image from only one high-energy image, both of which are acquired in a short time interval.

While the first and second image data are generated within a quite short time period (1-50 s) in the non-temporal dual-energy subtraction, the first and second image data are created at different points in time in the temporal dual-energy subtraction, which points in time can by all means be separated by multiple minutes. In the temporal dual-energy subtraction, multiple subtractions are implemented by means of high-energy slice image generated (or reconstructed) at time intervals, so a series of subtraction images is created with which the course of the contrast agent can be shown.

Stated differently, the present invention combines the contrast agent-assisted dual-energy tomosynthesis (CEDET, "Contrast-Enhanced Dual-Energy Tomosynthesis") with contrast agent-assisted mammography (CEDM, "Contrast-Enhanced Digital Mammography").

According to the invention, differentiation is made between the generation of two-dimensional images (mammography) and generation of the tomosynthesis image. Digital tomosynthesis is a combination of a digital image acquisition and image processing given a small movement of the x-ray tube or x-ray source. Tomosynthesis has certain similarities to computed tomography (CT) but is considered a separate technique by those in the art. In computed tomography, images are generated during a complete 360° revolution of the x-ray source around the examination subject, but in tomosynthesis the x-ray source pans only around the subject through a small angle (of 40°, for example), so only a small number of exposures (typically between 7 and 60) is created. By the use of high-resolution detectors, a very high resolution can be achieved in planes perpendicular to the Z-axis (axis in the direction of the tomosynthesis angle 0°, or the vertical direction, or the CC alignment), even though the resolution is lower in the direction of the Z-axis. The primary field of use of tomosynthesis is imaging of the female breast as a supplement to or replacement for mammography. In comparison to mammography, tomosynthesis operates with a lower radiation energy per projection. For example, given the same energy of individual x-ray photons, the total radiation energy (i.e. the sum of the radiation energies required to create all projections) of the tomosynthesis corresponds to one to two times the radiation energy to generate a two-dimensional image.

Corresponding information from earlier two-dimensional exposures and/or of earlier tomosynthesis scans is used in order to determine the x-ray energy to generate the two-dimensional low-energy image, the at least one two-dimensional high-energy image, and for the high-energy tomosynthesis scan.

For example, the two-dimensional low-energy image and the high-energy image or, respectively, images can be generated in the enrichment phase of the contrast agent in order to detect the rising edge of the contrast agent concentration. The high-energy tomosynthesis scan then represents the wash-out phase (falling edge of the contrast agent concentration). Since the enrichment phase is normally shorter than the wash-out phase, the two-dimensional images (the low-energy image and the at least one high-energy image) are used to detect the concentration of the contrast agent, or better to track the contrast agent concentration, since a few two-dimensional images can be generated in a shorter period of time than is necessary to implement a tomosynthesis scan.

For example, a time interval can be provided in which an enrichment of the contrast agent presumably occurs within the predetermined volume segment. The two-dimensional low-energy image and the at least one two-dimensional high-energy image are then automatically created in this time interval.

According to the invention, it is ensured that the two-dimensional low-energy image and the at least one two-dimensional high-energy image are generated in an enrichment phase of the contrast agent so that the non-temporal dual-energy subtraction allows conclusions about the contrast agent course in this enrichment phase.

A registration of the two-dimensional low-energy image and the at least one two-dimensional high-energy image advantageously occurs before the subtraction of the two-dimensional low-energy image of the at least one two-dimensional high-energy image, wherein an earlier two-dimensional low-energy image of the predetermined volume segment which was generated before the administration of the contrast agent is used for registration. This earlier two-dimensional low-energy image is normally an image which was created in an earlier examination of the patient.

By means of the registration, the images to be subtracted are advantageously adapted to one another and possible movements of the subject are corrected. The goal in the image registration is to find a transformation that brings the high-energy image into congruence with the low-energy image in the best possible manner. This prevents image regions that do not match one another from being subtracted from one another in the subtraction.

Via the use of an earlier two-dimensional low-energy image in the registration, movement artifacts, position-dependent subject changes and compression-dependent subject changes are advantageously compensated in the creation of the currently generated two-dimensional images.

According to the invention, it is possible for the two-dimensional low-energy image and/or the at least one high-energy image are created within the scope of the implementation of the high-energy tomosynthesis scan. For this, corresponding acquisition parameter settings (filter settings, tube voltage, tube current, acquisition duration) of the tomosynthesis apparatus and corresponding power supply parameters for an x-ray source of the tomosynthesis apparatus are produced given a change from tomosynthesis acquisition to acquisition of the two-dimensional low-energy image and/or of the at least one high-energy image. To continue the tomosynthesis scan, these altered filter settings and altered power supply parameters must again be changed to their settings for the tomosynthesis.

The generation of the two-dimensional images during the tomosynthesis advantageously enables the two-dimensional images to be created at an arbitrary point in time (thus not immediately before the tomosynthesis).

According to one embodiment according to the invention, the following Steps can be implemented in the following order:

1: Generate the two-dimensional low-energy image of the predetermined volume segment of an examination subject.
2. Generate the at least one high-energy image of the predetermined volume segment.
3. Generate an additional two-dimensional low-energy image of an additional volume segment of the examination subject.
4. Generate at least one additional high-energy image of the additional volume segment.
5. Implement an additional high-energy tomosynthesis scan of the additional volume segment.
6. Implement the high-energy tomosynthesis scan of the predetermined volume segment.

The additional two-dimensional low-energy image is subtracted from the additional high-energy images or from the multiple additional high-energy images in order to make the concentration of the contrast agent visible in the additional volume segment using the results or result images thereby generated via this additional non-temporal dual-energy subtraction. Image data of an earlier low-energy tomosynthesis scan of the additional volume segment can be subtracted from image data of the high-energy tomosynthesis scan of the additional volume segment within the scope of a temporal dual-energy subtraction in order to obtain corresponding results about the contrast agent course in the additional volume segment.

This embodiment according to the invention enables the examination of two different examination subjects (for example of a right breast and a left breast of a patient) with only a single administration of the contrast agent.

The temporal dual-energy subtraction—in which image data of the earlier low-energy tomosynthesis scan are subtracted from image data of the high-energy tomosynthesis scan—in particular requires a registration in which the image data of the earlier low-energy tomosynthesis scan are registered with the image data of the high-energy tomosynthesis scan, depending on the two-dimensional low-energy image.

By the use of the two-dimensional low-energy image in the registration, movement artifacts, positioning-dependent subject changes and compression-dependent subject changes can advantageously be compensated in the generation of the high-energy tomosynthesis scan.

Moreover, it is possible for a time interval to be provided in which a washing-out of the contrast agent is expected within the predetermined volume segment. The high-energy tomosynthesis is subsequently implemented automatically in this time interval in that parameters of the high-energy tomosynthesis (for example the number of projections to be generated or the time interval between the projections) is adapted such that the high-energy tomosynthesis can be implemented in the provided time interval.

According to an additional embodiment according to the invention, the following Steps can be implemented in the following order after the administration of the contrast agent:

1. Generate the two-dimensional low-energy image of the predetermined volume segment.
2. Generate an additional two-dimensional low-energy image of an additional volume segment.
3. Implement an additional high-energy tomosynthesis scan of the additional volume segment, wherein one or more additional two-dimensional high-energy images of the additional volume segment are thereby also generated.
4. Implement the high-energy tomosynthesis scan of the predetermined volume segment, wherein the one or more high-energy images of the predetermined volume segment are also generated.

The additional two-dimensional low-energy image is thereby also subtracted from the high-energy image or the respective additional high-energy images (non-temporal dual-energy subtraction). A temporal dual-energy subtraction of image data of an earlier low-energy tomosynthesis scan (which was implemented before the administration of the contrast agent with regard to the additional volume segment) from image data of the additional high-energy tomosynthesis scan of the additional volume segment can also be implemented.

The method according to the invention offers the following advantages:

A combination of a dual-energy imaging (difference from the two-dimensional low-energy image and the two-dimensional high-energy images) with a depiction of the chronological enrichment of the contrast agent and the wash-out phase (in particular via results of the high-energy tomosynthesis) is possible.

The contrast agent course can be determined very precisely via the generation of two-dimensional images in the temporally short enrichment phase.

A localization, for example of lesions and tumors, is also possible in three-dimensional space via the use of the high-energy tomosynthesis during the temporally longer (comparable to the enrichment phase) wash-out phase.

Within the scope of the present invention, an additional method is also provided to show a concentration of a contrast agent in a predetermined volume segment of an examination subject by means of a tomosynthesis apparatus. This additional method comprises the following Steps:

Provide a time interval in which an enrichment or a washing-out of the contrast agent within the predetermined volume segment is expected.

Automatically implement a tomosynthesis scan of the predetermined volume segment in the provided time interval. The concentration of the contrast agent in the predetermined volume segment is depicted or determined depending on the results of this tomosynthesis scan.

Because the tomosynthesis scan is adapted to the provided time interval or is synchronized with the provided time interval, both the contrast agent course in the enrichment phase and the contrast agent course in the wash-out phase are optimally shown and measured by means of the tomosynthesis scan. Due to the high coefficient of attenuation of the contrast agent, an image contrast of a possibly present malignant tumor is sufficient, even given the low radiation energy (in comparison to mammography or the generation of two-dimensional images) that is used to generate the projections during the tomosynthesis, to quantitatively determine the contrast agent concentration in the tumor (i.e. via corresponding pixel values). Since the projections generated during the tomosynthesis are acquired in succession, the contrast agent course can be shown and measured via the tomosynthesis scan.

For example, a number of exposures to be generated can be provided during a tomosynthesis scan. The time interval between two successive acquisitions of these exposures to be generated can be adapted to the provided time interval such that the provided number of exposures to be generated is generated within the predetermined time interval.

It is thereby ensured that the provided number of exposures to be generated is generated entirely during the enrichment phase or during the wash-out phase. Stated in a different way, the tomosynthesis scan can thereby advantageously be synchronized with the administration of the contrast agent so that the tomosynthesis scan takes place directly in the time interval of interest (i.e. across the entire enrichment phase or across the entire wash-out phase). In other words, the scan speed is adapted to the dynamic of the contrast agent, i.e. to the course of the contrast agent. According to the invention it is correspondingly taken into account that the enrichment of the contrast agent takes place relatively quickly (within approximately 10-50 s) so that a fast tomosynthesis scan (short interval between successive acquisitions) must be conducted. In contrast to this, the duration of the time curve of interest in the elimination of the contrast agent (wash-out phase) amounts to a few minutes. This means that the duration of the tomosynthesis scan is set so that this duration corresponds to the duration of the enrichment phase or, respectively, wash-out phase.

According to the invention, it is possible for both the enrichment phase and the wash-out phase to be tracked with a respective tomosynthesis scan. For this, a first time interval in which the enrichment of the contrast agent is expected within the predetermined volume segment and a second time interval in which the washing-out of the contrast agent is expected within the predetermined volume segment are provided. A first tomosynthesis scan is then implemented in the first time interval and a second tomosynthesis scan is implemented in the second time interval in order to show or to determine the concentration of the contrast agent in the predetermined volume segment, depending on the results of these two tomosynthesis scans. This means that the duration of the first tomosynthesis scan is set such that it corresponds to the first time interval and the duration of the second tomosynthesis scan is set such that it corresponds to the second time interval.

Starting from results of the tomosynthesis scan or scans, slice images of the predetermined volume segment can be reconstructed under consideration of a kinetic model of a flow of the contrast agent within the predetermined volume segment. The kinetic model is based on an equation system with differential terms to determine the propagation of the contrast agent in the enrichment phase and/or the wash-out phase. The kinetic model is known from CE-MRI ("Contrast Enhanced Magnet Resonance Imaging"); see "Imaging Systems for Medical Diagnostics"; A. Oppelt ISBN: 3-89578-226-2, Pages 660-667 and "Automatic identification and classification of characteristic kinetic curves of breast lesions on DCE-MRI; W. Chen et al.; Medical Physics, Vol. 33, No. 8, Aug. 2006; Pages 2878-2887. The kinetic model is known from pharmacokinetics and describes the concentration of the contrast agent as a function of time with conventional differential equations with parameters which describe the acquisition or, respectively, delivery of the contrast agent (pharmaceutical) in a compartment (vessel, cell, intracellular space). Pharmacokinetics, as a scientific sub-field of pharmacology, primarily researches and describes the effect of the body on an applied pharmaceutical or, respectively, (stated in a different way) its time curve in individual regions of the body.

By using the kinetic model in the reconstruction, variations due to different contrast agent concentrations at different points in time in the same volume segment can be taken into account in the reconstruction of three-dimensional image information of the predetermined volume segment from the projections created during the tomosynthesis.

Moreover, it is possible to reconstruct image data with an iterative reconstruction algorithm, starting from results of the tomosynthesis scan or scans. The iterative reconstruction algorithm can thereby contain a model of the contrast agent flow as a boundary condition of the projection images to be created. In other words, in the generation of the three-dimensional image information the iterative reconstruction algorithm accounts for the fact that different contrast agent concentrations (as a result of the contrast agent flow) prevail in the same volume segment at different points in time. For example, ART ("Algebraic Reconstruction Technique"), SART ("Simultaneous ART"), SIRT ("Simultaneous Iterative Reconstruction Technique"), ML ("Maximum Likelihood") or MAP ("Maximum Activity Projection") can be used as an iterative reconstruction algorithm.

In the event that only a few tomosynthesis scans are implemented (for example only two, namely a scan during the enrichment and a scan during the depletion), the total dose or total energy of the x-rays during the tomosynthesis scan according to the invention can be set to be higher by a predetermined factor (2, for example) than is normally the case in the implementation of a normal tomosynthesis.

By the increase of the total dose of the x-rays corresponding to the predetermined factor, the quality of the generated image data—and therefore the reliability of the quantitative image evaluation—can be increased.

Moreover, the contrast agent concentration in the predetermined volume segment can be determined from difference images. For this an image of the predetermined volume segment which was created by means of a tomosynthesis apparatus before an administration of the contrast agent is subtracted from an additional image which is reconstructed starting from results of the tomosynthesis implemented according to the invention in order to determine the concentration of the contrast agent in the predetermined volume segment via the corresponding difference image.

The further method according to the invention offers the following advantages:
- in comparison to magnetic resonance tomography, a higher spatial resolution and a higher temporal resolution can be realized specifically in the fast enrichment phase.
- In that the scan speed (i.e. the duration in which the tomosynthesis scan is implemented) is adapted to the contrast agent dynamic, the total radiation dose with which the patient is exposed can be kept optimally low.

It is noted that the method according to the invention and the further method according to the invention can be combined with one another. In particular, the further method according to the invention can be used to implement the high-energy tomosynthesis scan in the wash-out phase.

The present invention also encompasses a tomosynthesis apparatus with a detector and an x-ray source (in order to limit x-rays directed towards the detector) is also provided. An examination subject (in particular a female breast) can thereby be positioned between the x-ray source and the detector such that the x-rays traverse a predetermined volume segment of the examination subject before they strike the detector. The tomosynthesis apparatus has a controller to activate the x-ray source and the detector and an image computer in order to receive data of the predetermined volume segment (said data acquired by the detector) and to generate an image which shows a concentration of a contrast agent in the predetermined volume segment. After administration of a contrast agent, the tomosynthesis apparatus generates a two-dimensional low-energy image of the predetermined volume segment and at least one two-dimensional high-energy image of the predetermined volume segment, wherein a radiation energy to create a high-energy image is significantly higher than the radiation energy to create the low-energy image. Moreover, after the administration of the contrast agent the tomosynthesis apparatus implements a high-energy tomosynthesis of the predetermined volume segment, wherein a total radiation dose of the high-energy tomosynthesis is significantly higher than a radiation dose to create the two-dimensional low-energy image. With the aid of the image computer, the controller subtracts the two-dimensional low-energy image from each high-energy image (non-temporal dual-energy subtraction) in order to generate a result or, respectively, result image in which the concentration of the contrast agent can be shown.

The advantages of the tomosynthesis apparatus according to the invention substantially correspond to the advantages of the corresponding method according to the invention as described above.

Within the scope of the present invention, an additional tomosynthesis apparatus with a detector and an x-ray source for the emission of x-rays directed toward the detector is also provided. In this additional tomosynthesis apparatus an examination subject (in particular a female breast) can be positioned between the x-ray source and the detector such that the x-rays traverse a predetermined volume segment of said examination subject before they strike the detector. The additional tomosynthesis apparatus also has a controller to activate the x-ray source and the detector, as well as an image computer in order to receive data of the predetermined volume segment (said data acquired by the detector) and generate an image from which a concentration of a contrast agent in the predetermined volume segment can be derived. A time interval in which an enrichment or a washing-out of the contrast agent within the predetermined volume segment is expected can be provided to the controller. Within the provided time interval, the tomosynthesis apparatus implements a tomosynthesis in order to determine the concentration of the contrast agent in the predetermined volume segment depending on results of this tomosynthesis (the result is in particular an image).

The advantages of the additional tomosynthesis apparatus according to the invention significantly correspond to the advantages of the additional method according to the invention which are stated in detail in the preceding, such that a repetition is omitted here.

Furthermore, the present invention encompasses a non-transitory computer-readable storage medium encoded with programming instructions or control commands (software), which can be loaded into a memory of a programmable controller or a computer of a tomosynthesis apparatus. All or various embodiments of the methods according to the invention that are described in the preceding can be executed by when the computer program in the controller or control device of the tomosynthesis apparatus according to the encoded information. The programming instruction may require other items (libraries and auxiliary functions, for example) in order to realize the corresponding embodiments of the methods. The software can be source code (C++, for example) that must still be compiled (translated) and linked or that only needs to be interpreted, or can be an executable software code that has only to be loaded into the corresponding computer for execution.

The electronically readable data medium can be, for example, a DVD, a magnetic tape or a USB stick,—on which is stored electronically readable control information, in particular software (see above).

The present invention is particularly suitable to supplement or extend contrast agent-assisted mammography. Naturally, the present invention is not limited to this preferred field of application since contrast agent courses or contrast agent concentrations in other regions of the body of a living organism can also be shown with the present invention.

DESCRIPTION OF THE PREFERRED EMBODIMENTS

Figure 1:
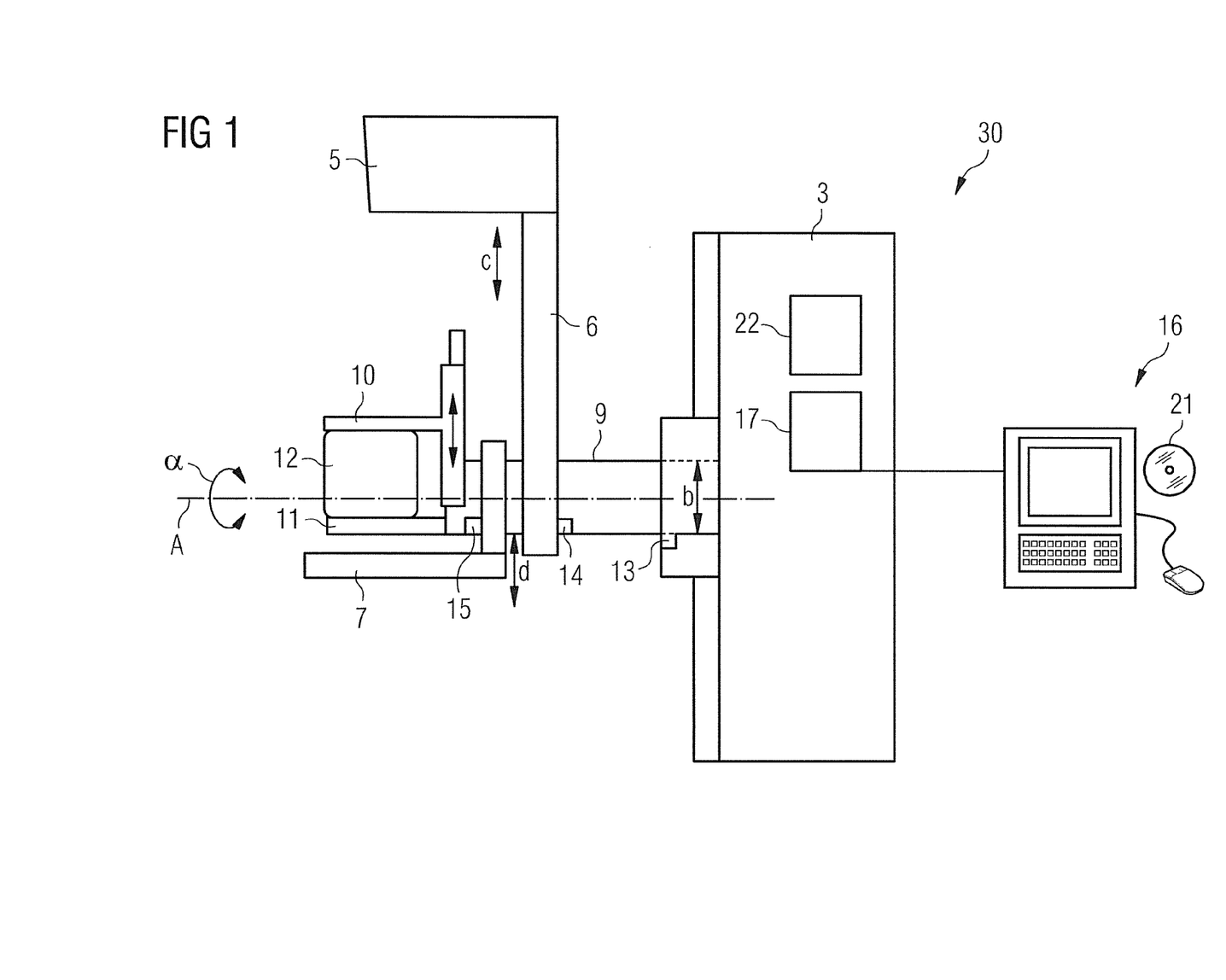
FIG. 1 schematically depicts a tomosynthesis apparatus according to the invention.

A tomosynthesis apparatus 30 according to the invention for mammography examinations is schematically shown in FIG. 1. The tomosynthesis apparatus 30 has a support arm 9 that is mounted such that it can pivot in a bearing around a horizontal axis A (see double arrow and angle α). The bearing is arranged on a stand 3 and can be vertically adjusted as indicated with the double arrow b. An arm 6 provided with an x-ray source 5, a flat panel detector 7 and a compression device (consisting of a compression plate 10 and a support plate 11) are arranged on the support arm 9. Schematically shown in FIG. 1 is a female breast 12 compressed by the compression plate 10 and the bearing plate 11. The arm 6 can pivot around the axis A relative to the support arm 1, the detector 7 and the compression device 10, 11. Electromotors 13 through 15 of the tomosynthesis apparatus 30 are provided for height adjustments and pivot motions.

A control of the tomosynthesis apparatus 30 takes place via an operating device 6 of the tomosynthesis apparatus 30 which is connected with a controller 17 and an image computer 22 of said tomosynthesis apparatus 30. Specific methods (among these the methods according to the invention) can be loaded into the controller 17 and the operating device 16 by means of a DVD 21.

Figure 2:
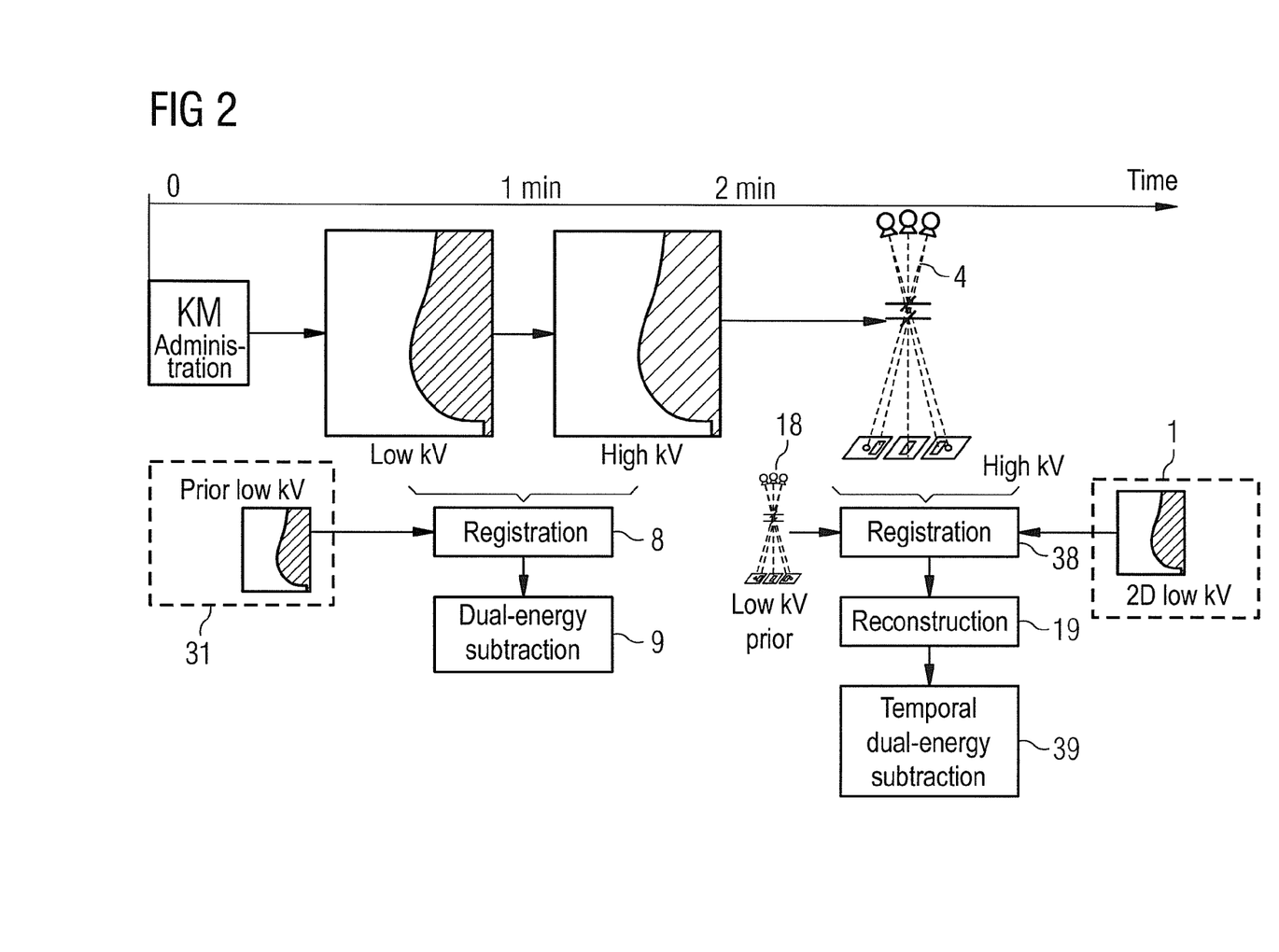
FIG. 2 shows a workflow according to the invention of a dual-energy image acquisition, image processing and presentation, beginning with the contrast agent administration.

A basic workflow according to the invention of a dual-energy image acquisition, image processing and image presentation is shown in FIG. 2, beginning with the contrast agent administration. After the administration of the contrast agent, the acquisition of a two-dimensional low-energy image 1 of the female breast (of the predetermined volume segment) most often takes place in the form of a standard screening projection (CC or MLO). Multiple two-dimensional high-energy images 2 are subsequently generated with the same acquisition angle (CC or MLO) of the female breast. A registration of the low-energy image 1 with a respective one of the high-energy images 2 takes place using earlier low-energy images 31 of the same breast of the patient. After this registration 8 the low-energy image 1 is subtracted from each of the high-energy images 2, so a dual-energy image (difference image) results for each subtraction. This subtraction is also designated as a non-temporal dual-energy subtraction. The concentration of the contrast agent is visible in each of these difference images, such that the contrast agent course results from the multiple difference images.

The acquisition of the two-dimensional low-energy image 1 and the acquisition of the two-dimensional high-energy images 2 take place in the enrichment phase of the contrast agent since the generation of the two-dimensional images 1, 2 can take place fast enough in order to generate these two-dimensional images 1, 2 even given a temporally short enrichment phase of only 10 s.

After the creation of the two-dimensional high-energy images 2 (approximately 2 to 4 minutes after the contrast agent administration), a high-energy tomosynthesis 4 of the same breast is implemented. With the use of the two-dimensional low-energy image 1, the image data resulting from the high-energy tomosynthesis 4 are registered with image data of an earlier low-energy tomosynthesis 18 implemented with regard to the same breast.

After the registration 38, the image data of the high-energy tomosynthesis 4 that are created from different tomosynthesis angles are adapted to one another such that a three-dimensional image data set of the female breast is created. A subtraction 39 subsequently occurs in which the image data of the earlier low-energy tomosynthesis 18 are subtracted from the image data of the high-energy tomosynthesis 4, which is also known as a temporal dual-energy subtraction.

The high-energy tomosynthesis 4 occurs in the wash-out phase in which the contrast agent flows out of the lesions or tumors, such that the concentration of the contrast agent decreases. This wash-out phase normally has a smaller (negative) slope of the contrast agent concentration per time unit in comparison to the (positive) slope of the contrast agent concentration in the enrichment phase, such that more time is available to implement the high-energy tomosynthesis.

Figure 3:
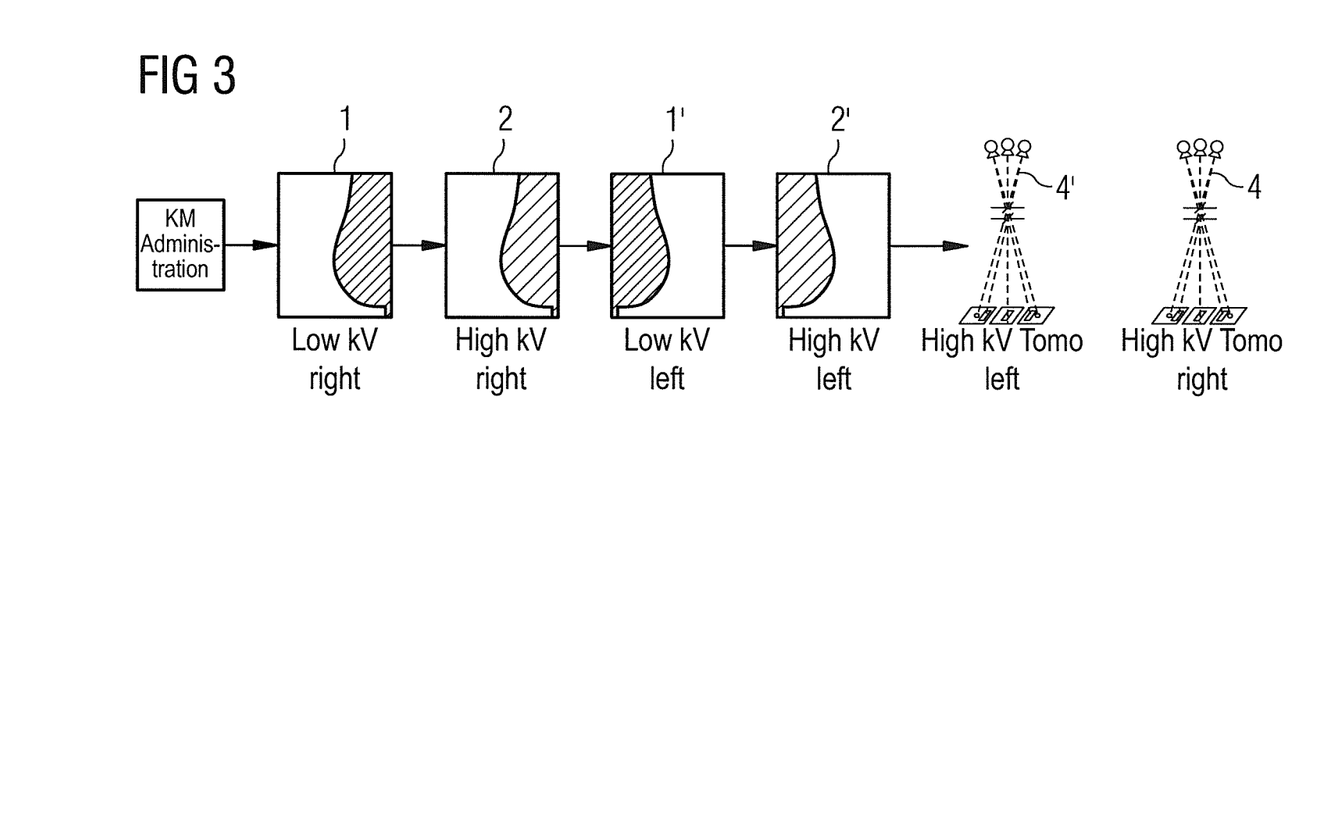
FIG. 3 shows a further workflow according to the invention of a dual-energy image acquisition, image processing and presentation, beginning with the contrast agent administration, wherein two different volume segments are examined.

An additional workflow according to the invention of a dual-energy image acquisition, image processing and presentation is shown in FIG. 3, beginning with the contrast agent administration, wherein two different volume segments (both breasts) are examined.

After the administration of the contrast agent, a two-dimensional low-energy image is first created from the right breast of the patient and multiple two-dimensional high-energy images 2 are subsequently created. The right breast is subsequently released and a two-dimensional low-energy image 1' (and following this multiple two-dimensional high-energy images 2') of the left breast is created. After the generation of the two-dimensional high-energy images 2', a high-energy tomosynthesis scan 4' of the left breast is implemented. The left breast is subsequently released and a high-energy tomosynthesis scan 4 of the right breast is implemented.

With the method shown in FIG. 3, both breasts of a patient can accordingly be examined with the with the same administration of a contrast agent. Since a low-energy image 1, 1' of multiple high-energy images 2, 2' and a high-energy tomosynthesis scan 4, 4' are thus created both for the right breast and for the left breast, a non-temporal dual-energy subtraction 9 and a temporal dual-energy subtraction 39 can be implemented for both the right breast and the left breast, as is shown in detail for one breast in FIG. 2.

Figure 4:
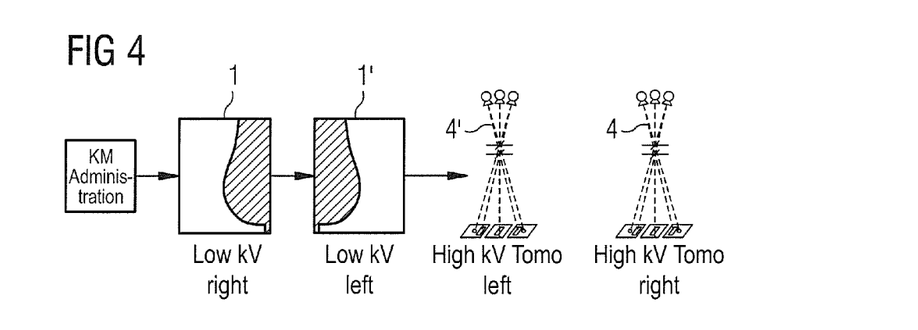
FIG. 4 shows a different workflow according to the invention of a dual-energy image acquisition, image processing and presentation, beginning with the contrast agent administration, wherein two different volume segments are examined.

A variant of the workflow according to the invention shown in FIG. 3 for the examination of both breasts is shown in FIG. 4. In comparison to the workflow shown in FIG. 3, the generation of the two-dimensional high-energy images 2, 2' of the right and left breast is missing in the workflow shown in FIG. 4, so the generation of the two-dimensional images 1, 1' takes place more quickly and the high-energy tomosynthesis scan 4, 4' can be started faster. The two-dimensional high-energy images 2' of the left breast are generated during the high-energy tomosynthesis scan 4' of the left breast while the two-dimensional high-energy images 2 of the right breast are generated during the high-energy tomosynthesis scan 4 of the right breast.

Figure 5:
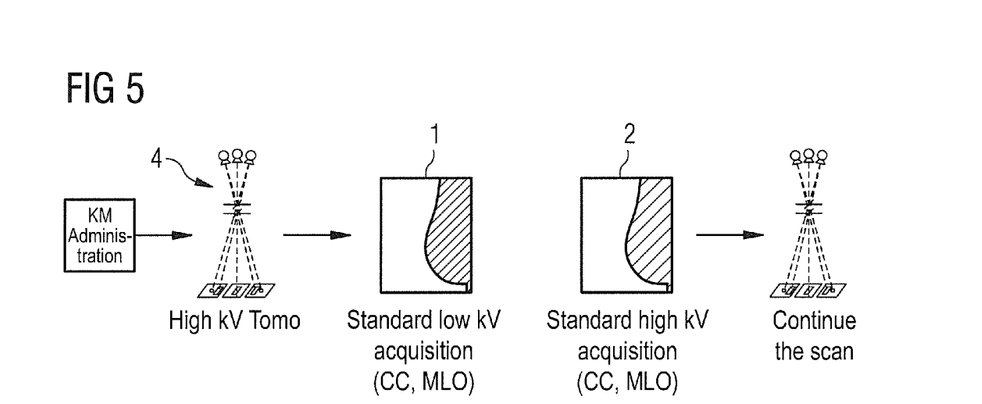
FIG. 5 shows a workflow according to the invention for the generation of two-dimensional images during a high-energy tomosynthesis scan.

A variant of the embodiment shown in FIG. 2 is depicted in FIG. 5. In the embodiment shown in FIG. 5, the high-energy tomosynthesis scan 4 begins directly after the administration of the contrast agent. The two-dimensional low-energy image 1 and the multiple two-dimensional high-energy images 2 are generated during this high-energy tomosynthesis scan 4.

Figures 6, 6A:
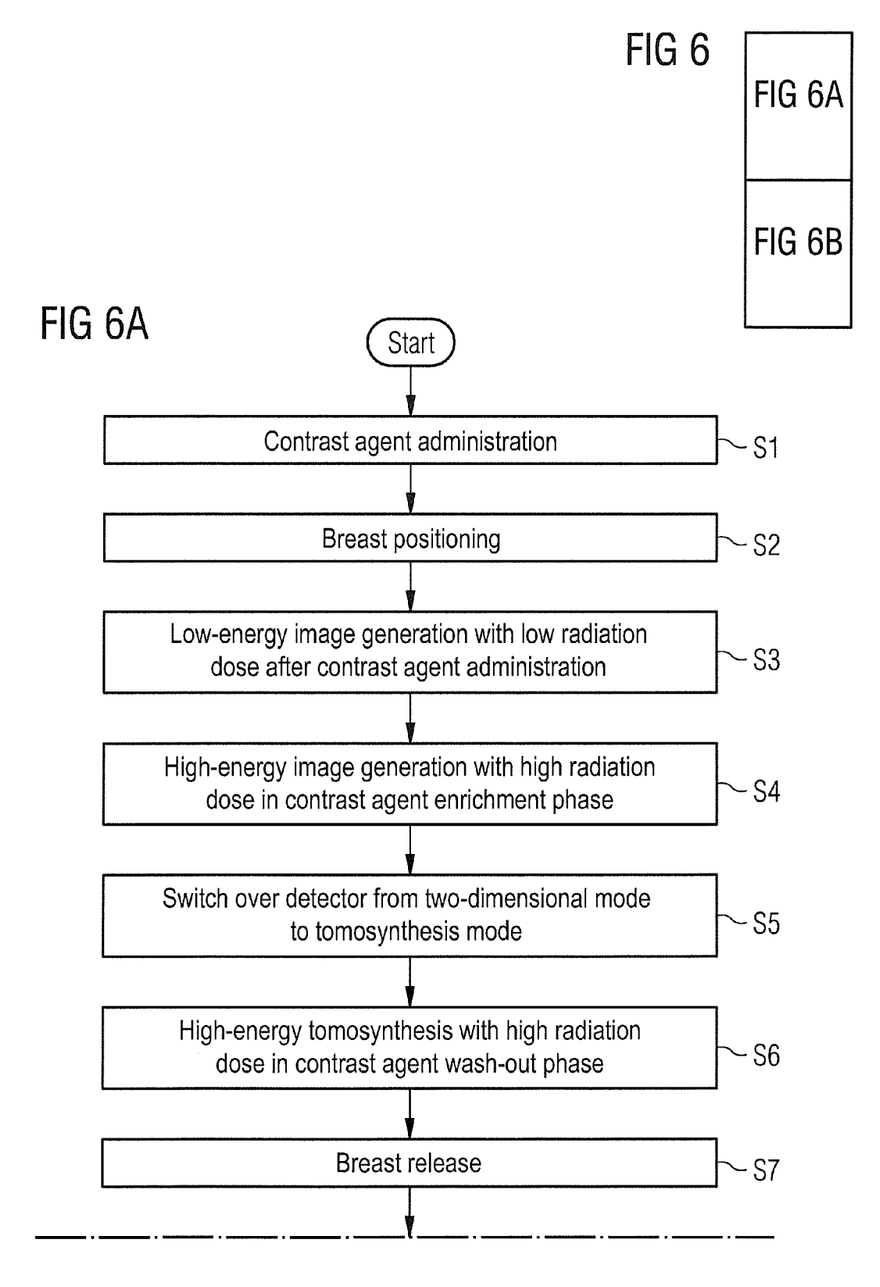
FIGS. 6a and 6b together show a flow chart of a method according to the invention.

A flow chart diagram of an embodiment of the method according to the invention is presented in FIG. 6a.

In a first Step S1, a contrast agent is administered to the patient before the breast to be examined is positioned between the bearing plate and the compression plate in a second Step S2. These two first Steps S1 and S2 can also be swapped in terms of their order so that the contrast agent is only administered when the breast to be examined is already positioned between the bearing plate and the compression plate.

In the following Step S3 a two-dimensional low-energy image is subsequently generated with a correspondingly low x-ray energy as quickly as possible after the administration of the contrast agent. During the enrichment phase of the contrast agent in possible tumors and lesions present in the breast, multiple two-dimensional high-energy images are generated with a correspondingly high x-ray energy in Step S4.

Since the generation of the two-dimensional images (mammography) is concluded, in Step S5 the detector is switched over from two-dimensional mode into a tomosynthesis mode. In Step S6 a high-energy tomosynthesis scan is subsequently implemented with a correspondingly high radiation energy in order to generate image data of the wash-out phase of the contrast agent before the breast is released in Step S7.

Figure 6B:
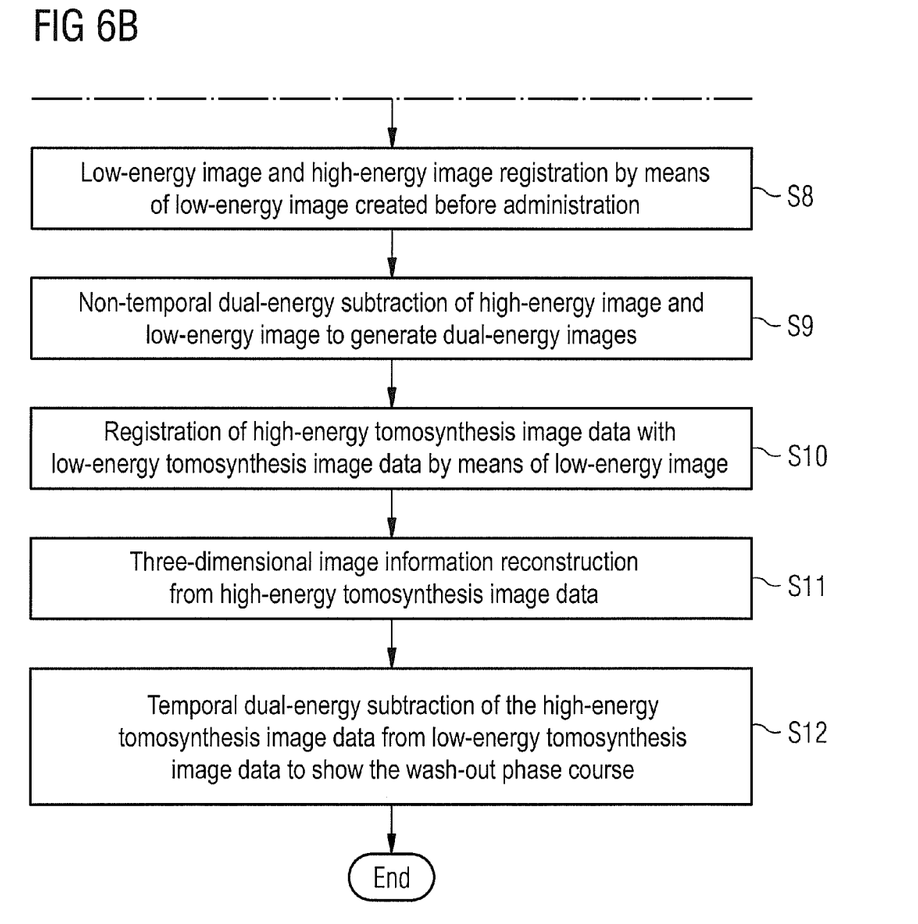

The processing of the images or image data generated in Steps S1 through S7 takes place in the Steps shown in FIG. 6b. Steps S8 through S12 can thereby also be implemented in a different order than as shown in FIG. 6b insofar as the registration of the corresponding images or image data occurs before a reconstruction or subtraction of these images or image data. Moreover, Steps S8 through S12 do not need to occur after Steps S1 through S7; rather, these can be interleaved with these Steps S1 through S7 insofar as the images or image data required for a processing Step S8 through S12 are created beforehand via the corresponding generation Steps S3, S4, S6.

In Step S8 the two-dimensional low-energy image 1 is registered with each of the high-energy images 2, wherein this registration is implemented depending on a three-dimensional low-energy image created before the administration of the contrast agent. In Step S9 the low-energy image is subsequently subtracted from each high-energy image, whereby a number of dual-energy images or reference images is created which corresponds to the number of two-dimensional high-energy images. The respective subtraction of the low-energy image from the respective high-energy image is also designated as non-temporal dual-energy subtraction.

In Step S10 the image data of the high-energy tomosynthesis scan are registered with image data of a low-energy tomosynthesis scan implemented before the administration of the contrast agent, wherein this registration is implemented depending on the two-dimensional low-energy image generated in Step S3. In Step S11, three-dimensional image information of the examined breast is reconstructed from the projections generated in the high-energy tomosynthesis scan. Arbitrary slice images (with arbitrary viewing angles) of the examined breast can be generated with the aid of this three-dimensional image information. To show the contrast agent concentration or the course of the contrast agent concentration in the wash-out phase, the image data of the earlier low-energy tomosynthesis scan are subtracted from the image data of the high-energy tomosynthesis scan (which is also known as a temporal dual-energy subtraction).

Although modifications and changes may be suggested by those skilled in the art, it is the intention of the inventors to embody within the patent warranted hereon all changes and modifications as reasonably and properly come within the scope of their contribution to the art.

We claim as our invention:

1. A method to visually present a concentration of a contrast agent in a predetermined volume segment of an examination subject, comprising:
    administering a contrast agent to an examination subject and thereafter operating an imaging apparatus with a low radiation energy to generate a two-dimensional, low-energy image of a predetermined volume segment of an examination subject;
    also after administering the contrast agent, operating the imaging apparatus with a high radiation energy, which is substantially higher than said low radiation energy, to generate at least one two-dimensional, high-energy image of the predetermined volume segment;
    after generating said two-dimensional, low-energy image, operating the imaging apparatus with a high total radiation energy that is substantially higher than said low radiation energy, to implement a high-energy tomosynthesis of the predetermined volume segment, thereby obtaining a three-dimensional tomosynthesis image;
    in a processor, subtracting said two-dimensional, low-energy image from said at least one two-dimensional, high-energy image to generate a subtraction image in which a concentration of said contrast agent in said predetermined volume segment is visible; and
    making each of said tomosynthesis image and said subtraction image available in a form for visual display thereof.

2. A method as claimed in claim 1 comprising when subtracting said two-dimensional, low-energy image from said at least one two-dimensional, high-energy image, bringing said two-dimensional, high-energy image and said at least one two-dimensional, high-energy image into registration with each other dependent on a previous two-dimensional image of said predetermined volume segment acquired before administering said contrast agent.

3. A method as claimed in claim 1 wherein a time interval exists in which enrichment of the contrast agent occurs within the predetermined volume segment and comprising automatically triggering generation of said two-dimensional, low-energy image and said at least one two-dimensional, high-energy image in said time interval.

4. A method as claimed in claim 1 wherein said imaging apparatus comprises an x-ray source supplied with power from a power supply according to power supply parameters, and comprising generating corresponding acquisition parameter settings for said imaging apparatus and power supply parameters for said x-ray source, respectively for generating said two-dimensional, low-energy image and for said high-energy tomosynthesis, upon changing between operation of said imaging apparatus for generating said two-dimensional, low-energy image and for generating said high-energy tomosynthesis, and vice versa.

5. A method as claimed in claim 1 wherein said imaging apparatus comprises an x-ray source supplied with power from a power supply according to power supply parameters, and comprising generating corresponding acquisition parameter settings for said imaging apparatus and power supply parameters for said x-ray source, respectively for generating said at least one two-dimensional, high-energy image and for said high-energy tomosynthesis, upon changing between operation of said imaging apparatus for generating said at least one two-dimensional, high-energy image and for generating said high-energy tomosynthesis, and vice versa.

6. A method as claimed in claim 1 comprising implementing the following steps in the following order:
    a) generate the two-dimensional low-energy image of the predetermined volume segment,
    b) generate the at least one two-dimensional high-energy image of the predetermined volume segment,
    c) generate an additional two-dimensional low-energy image of an additional predetermined volume segment of said examination subject with the low radiation energy,
    d) generate at least one additional two-dimensional high-energy image of the additional predetermined volume segment with the high radiation energy,
    e) implement an additional high-energy tomosynthesis of the additional predetermined volume segment with the high total radiation energy,
    f) implement the high-energy tomosynthesis of the predetermined volume segment, and
    the additional two-dimensional low-energy image is also subtracted from the at least one additional high-energy image in order to generate an additional result with which the concentration of the contrast agent in the additional volume segment is visible.

7. A method as claimed in claim 1 comprising implementing the following steps in the following order:
    a) generate the two-dimensional low-energy image of the predetermined volume segment,
    b) generate an additional two-dimensional low-energy image of an additional predetermined volume segment of said examination subject with the low radiation energy,
    c) implement an additional high-energy tomosynthesis of the additional predetermined volume segment with the high total radiation energy, wherein during the high-energy tomosynthesis at least one additional two-dimensional high-energy image of the additional predetermined volume segment is generated with the high radiation energy,
    d) implement the high-energy tomosynthesis, wherein the at least one two-dimensional high-energy image is created during the high-energy tomosynthesis, and
    the additional two-dimensional low-energy image is also subtracted from the at least one additional two-dimensional high-energy image in order to generate an additional result with which the concentration of the contrast agent in the additional predetermined volume segment is visible.

8. A method as claimed in claim 1 wherein a time interval exists in which a washing-out of the contrast agent occurs within the predetermined volume region, and automatically triggering said high-energy tomosynthesis in said time interval.

9. A method as claimed in claim 1 comprising implementing a temporal dual-energy subtraction between image data of the high-energy tomosynthesis and image data of a previous low-energy tomosynthesis acquired before administering said contrast agent, with a low total radiation energy that is substantially lower than said high total radiation energy.

10. A method as claimed in claim 9 comprising, in said temporal dual-energy subtraction, bringing said image data of said high-energy tomosynthesis and the image data of the previous low-energy tomosynthesis into registration with each other.

11. A method to visually present a concentration of a contrast agent in a predetermined volume segment of an examination subject, comprising:
 administering contrast agent to an examination subject and identifying a time interval in which an enrichment or a washing-out of the contrast agent occurs in a predetermined volume segment of the examination subject;
 automatically respectively triggering acquisition of sets of tomosynthesis image data from said predetermined volume segment in said time interval and, from said tomosynthesis image data, generating a visual presentation in which a concentration of said contrast agent in said predetermined volume is visible; and
 acquiring said sets of tomosynthesis image data with respective time separations therebetween, and adapting said time separation between two chronologically successively acquired sets of said tomosynthesis image data to said time interval to allow said plurality of tomosynthesis image data sets to be acquired within said time interval.

12. A method as claimed in claim 11 wherein said time interval comprises a first time interval in which said enrichment of said contrast agent occurs within the predetermined volume segment, and a second time interval in which said washing-out of said contrast agent occurs within said predetermined volume segment, and comprising acquiring said tomosynthesis image data by implementing a first tomosynthesis in said first time interval and implementing a second tomosynthesis in said second time interval, and visually presenting said concentration of said contrast agent in said predetermined volume segment dependent on image data acquired in said first tomosynthesis and said second tomosynthesis.

13. A method as claimed in claim 11 comprising reconstructing slice images of said predetermined volume segment in a processor, using said tomosynthesis image data and a kinetic model of flow of said contrast agent in said predetermined volume segment.

14. A method as claimed in claim 11 comprising reconstructing an image of said predetermined volume segment in a processor by implementing an iterative reconstruction algorithm in said processor starting from said tomosynthesis image data and using a model of flow of said contrast agent in said predetermined volume segment as a boundary condition in said iterative reconstruction algorithm.

15. A method as claimed in claim 11 comprising acquiring said tomosynthesis image data set with a total radiation energy of x-rays that is larger by a predetermined factor than radiation energy of x-rays during a conventional tomosynthesis.

16. A method as claimed in claim 11 comprising generating an image of said predetermined volume segment using previous tomosynthesis image data acquired before administering said contrast agent to said examination subject, and subtracting said image of the predetermined volume segment generated from said previous tomosynthesis image data from an image of the predetermined volume segment reconstructed from said tomosynthesis image data after administering said contrast agent, in order to visually present said concentration of said contrast agent in said predetermined volume segment.

17. An imaging apparatus to visually present a concentration of a contrast agent in a predetermined volume segment of an examination subject, comprising:
 a contrast agent administration unit;
 an imaging apparatus;
 a control unit configured to operate the contrast agent administration unit to administer a contrast agent to an examination subject and thereafter operate the imaging apparatus with a low radiation energy to generate a two-dimensional, low-energy image of a predetermined volume segment of an examination subject;
 also after administering the contrast agent, said control unit being configured to operate the imaging apparatus with a high radiation energy, which is substantially higher than said low radiation energy, to generate at least one two-dimensional, high-energy image of the predetermined volume segment;
 after generating said two-dimensional, low-energy image, said control unit being configured to operate the imaging apparatus with a high total radiation energy that is substantially higher than said low radiation energy, to implement a high-energy tomosynthesis of the predetermined volume segment, thereby obtaining a three-dimensional tomosynthesis image; and
 a processor configured to subtract said two-dimensional, low-energy image from said at least one two-dimensional, high-energy image to generate a subtraction image in which a concentration of said contrast agent in said predetermined volume segment is visible, and to make each of said tomosynthesis image and said subtracting image available in a form for visual display thereof.

18. An imaging apparatus to visually present a concentration of a contrast agent in a predetermined volume segment of an examination subject, comprising:
 a contrast agent administration unit;
 an imaging apparatus;
 a control unit configured to operate the contrast agent administration unit to administer contrast agent to an examination subject and identify a time interval in which an enrichment or a washing-out of the contrast agent occurs in a predetermined volume segment of the examination subject;
 said control unit being configured to automatically respectively trigger acquisition of sets of tomosynthesis image data from said predetermined volume segment in said time interval;
 said control unit being configured to acquire said sets of tomosynthesis image data with respective time separations therebetween, and adapting said time separation between two chronologically successively acquired sets of said tomosynthesis image data to said time interval to allow said plurality of tomosynthesis image data sets to be acquired within said time interval; and
 a processor configured to generate, from said tomosynthesis image data, a visual presentation in which a concentration of said contrast agent in said predetermined volume is visible.

19. A non-transitory computer-readable storage medium encoded with programming instructions, said storage medium being loaded into a computerized controller of an imaging apparatus having a contrast agent and administration unit, and said programming instructions causing said computerized controller to:

operate the contrast agent and administration unit to administer a contrast agent to an examination subject and thereafter operate the imaging apparatus with a low radiation energy to generate a two-dimensional, low-energy image of a predetermined volume segment of an examination subject;

also after administering the contrast agent, operate the imaging apparatus with a high radiation energy, which is substantially higher than said low radiation energy, to generate at least one two-dimensional, high-energy image of the predetermined volume segment;

after generating said two-dimensional, low-energy image, operate the imaging apparatus with a high total radiation energy that is substantially higher than said low radiation energy, to implement a high-energy tomosynthesis of the predetermined volume segment, thereby obtaining a three-dimensional tomosynthesis image;

subtract said two-dimensional, low-energy image from said at least one two-dimensional, high-energy image to generate a subtraction image in which a concentration of said contrast agent in said predetermined volume segment is visible; and make each of said tomosynthesis image and said subtraction image available in a form for visual display thereof.

20. A non-transitory computer-readable storage medium encoded with programming instructions, said storage medium being loaded into a computerized controller of an imaging apparatus having a contrast agent administration unit, and said programming instructions causing said computerized controller to:

operate the contrast agent and administration unit to administer contrast agent to an examination subject and identifying a time interval in which an enrichment or a washing-out of the contrast agent occurs in a predetermined volume segment of the examination subject; and operate the imaging apparatus by automatically respectively triggering acquisition of sets of tomosynthesis image data from said predetermined volume segment in said time interval;

acquire said sets of tomosynthesis image data with respective time separations therebetween, and adapting said time separation between two chronologically successively acquired sets of said tomosynthesis image data to said time interval to allow said plurality of tomosynthesis image data sets to be acquired within said time interval; and from said tomosynthesis image data, generate a visual presentation in which a concentration of said contrast agent in said predetermined volume is visible.

* * * * *